United States Patent [19]

Ozawa et al.

[11] Patent Number: 5,446,226
[45] Date of Patent: Aug. 29, 1995

[54] PROCESS FOR PRODUCING DIMETHYLNAPHTHALENE

[75] Inventors: Shinji Ozawa; Makoto Takagawa; Takayasu Fujimori, all of Tsukuba, Japan

[73] Assignee: Mitsubishi Gas Chemical Company, Inc., Tokyo, Japan

[21] Appl. No.: 156,402

[22] Filed: Nov. 19, 1993

Related U.S. Application Data

[63] Continuation of Ser. No. 2,920, Jan. 11, 1993, abandoned.

[30] Foreign Application Priority Data

Feb. 3, 1992 [JP] Japan ................. 4-047545

[51] Int. Cl.$^6$ ............................................. C07C 5/00
[52] U.S. Cl. ........................... 585/411; 585/407; 585/418; 585/419
[58] Field of Search ............ 585/407, 411, 418, 419

[56] References Cited

U.S. PATENT DOCUMENTS

| 5,008,479 | 4/1991 | Abe et al. ................. 585/320 |
| 5,043,501 | 8/1991 | Del Rossi et al. ........... 585/323 |

FOREIGN PATENT DOCUMENTS

| 50-001036 | 1/1975 | Japan . |
| 50-001037 | 1/1975 | Japan . |
| 50-017983 | 6/1975 | Japan . |
| 50-017985 | 6/1975 | Japan . |
| 50-022551 | 7/1975 | Japan . |
| 52-047460 | 2/1977 | Japan . |

OTHER PUBLICATIONS

Database WPI, Section Ch, Week 7539, Derwent Publications Ltd., London, GB; Class B05, AN 75-64848W of JP-B-50 026 533 (Teijin KK) 1 Sep. 1975.
Database WPI, Section Ch, Week 7529, Derwent Publications Ltd., London, GB; Class E14, AN 75-48770W of JP-B-50 017 983 (Teijin KK) 25 Jun. 1975.
Database WPI, Section Ch, Week 7506, Derwent Publications Ltd., London, GB; Class E14, AN 75-10101W of JP-B-50 001 037 (Teijin Ltd) 14 Jan. 1975.
Database WPI, Section Ch. Week 7506, Derwent Publications Ltd., London, GB; Class E14, AN 75-10100W of JP-B-50 001 036 (Teijin Ltd) 14 Jan. 1975.
Datbase WPI, Section Ch, Derwent Publications Ltd., London, GB; Class E14, AN 73-76504U of JP-A-48 067 261 (Teijin Ltd) 1973.

*Primary Examiner*—P. Achutamurthy
*Attorney, Agent, or Firm*—Frishauf, Holtz, Goodman & Woodward

[57] ABSTRACT

A process for efficiently producing dimethylnaphthalene by a single-step reaction which comprises cyclizing dehydrogenating 5-tolyl-penta-2-ene in the presence of a catalyst comprising in combination (a) a solid acid such as crystalline aluminosilicate, silica-alumina or alumina; (b) a noble metal such as palladium and platinum; and a carrier such as carbon, silicon oxide, titanium oxide and zirconium oxide. The process results in simplification of production, effective utilization of reaction heat and rationalization of the heat balance.

18 Claims, No Drawings

PROCESS FOR PRODUCING DIMETHYLNAPHTHALENE

This application is a Continuation of application Ser. No. 08/002,920, filed Jan. 11, 1993, abandoned.

BACKGROUND OF THE INVENTION

1. Field of the Invention

The present invention relates to a process for producing dimethylnaphthalene (hereinafter sometimes abbreviated to "DMN"). DMN is a compound of utmost importance as a starting raw material for naphthalene dicarboxylic acid to be used in the production of plastics such as polyesters. For example, polyethylene 2,6-naphthalene dicarboxylate which is produced from 2,6-naphthalene dicarboxylic acid and ethylene glycol has heat resistance and mechanical properties more favorable than those of polyethylene terephthalate and is used for producing films and fibers.

2. Description of the Related Art

Isomerically high purity is required for naphthalene dicarboxylic acid and DMN as starting raw materials for plastics. Specifically DMN has 10 isomers according to the positions of the methyl groups, including 1,2-, 1,3-, 1,4-, 1,5-, 1,6-, 1,7-, 1,8-, 2,3-, 2,6- and 2,7-DMN and, when used as the starting raw material for naphthalene dicarboxylic acid, it is required to be a specific DMN free from other position isomers.

As the process for producing DMN, there are available an isolation process from a high boiling fraction in a petroleum refinery or the tar fraction of coal origin, an alkylation process of naphthalene, a synthetic process using an alkylbenzene and an olefin and the like.

In the case of the isolation process from a high boiling fraction in a petroleum refinery or the tar fraction of coal origin, each of the fractions is a mixture of various DMN isomers and therefore, is required to be isomerized and isolated from the resultant isomers for the purpose of obtaining the specific desired DMN from the isomers mixture. With regard to isomerization, it is well-known that the above-mentioned 10 DMN isomers are classified into 4 groups including A to D groups as mentioned hereinbelow and that the isomerization in the same group is relatively easy, whereas among different groups isomerization is difficult. In addition, it is extremely difficult to isolate the specific desired DMN from various DMN isomers. Furthermore, a variety of components other than DMN contained in the above-mentioned fractions makes it extremely difficult to isolate and recover the specific desired DMN in high purity from the mixture of DMN and the others.

Group A - - - 1,5-DMN; 1,6-DMN; and 2,6-DMN
Group B - - - 1,7-DMN; 1,8-DMN; and 2,7-DMN
Group C - - - 1,3-DMN; 2,3-DMN; and 1,4-DMN
Group D - - - 1,2-DMN The alkylation process of naphthalene is put into practice usually by using a solid acid as the catalyst such as zeolite and silica-alumina. The process, however, involves the problems in that there are produced monomethylnaphthalene, trimethylnaphthalene, etc. other than DMN, a high selectivity to DMN is not attained and the resultant DMN is a mixture of a number of isomers. Accordingly, the process makes it difficult to afford the specific desired DMN in high yield as is the case with the isolation process from a high boiling fraction in a petroleum refinery or the tar fraction of coal origin.

As the countermeasure against the aforementioned problems, there is available a process for producing a specific DMN from an alkylbenzene and an olefin through multistage steps, exemplified by Japanese Patent Application Laid-Open No. 96540/1990 in which 2,6-DMN is produced from m-xylene, propylene and carbon monoxide and U.S. Pat. No. 5,008,479 in which 2,6-DMN is produced from toluene, butene and carbon monoxide.

Similarly, Japanese Patent Application Laid-Open Nos. 134634/1974, 89353/1975 and 67261/1974 disclose a process for producing 5-(o-tolyl)-penta-2-ene from o-xylene and butadiene, a process for producing 1,5-dimethyltetralin by cyclizing 5-(o-tolyl)-penta-2-ene and a process for producing 1,5-DMN by dehydrogenating 1,5-dimethyltetralin, respectively. The combination of the above-disclosed processes enables the production of 1,5-DMN with isomerically high purity from o-xylene and butadiene.

Japanese Patent Application Laid-Open No. 503389/1989 discloses a process for producing highly pure 2,6-DMN by isomerizing 1,5-DMN into the mixture of 1,5-DMN, 1,6-DMN and 2,6-DMN, which mixture is crystallized into the objective 2,6-DMN. The aforesaid process is highly advantageous in that isomerization and crystallization are carried out among 3 DMN isomers belonging to the same group as compared with those among the isomers belonging to different groups.

2,6-DMN has attracted the highest attention recently among the DMN isomers as the starting raw material for 2,6-naphthalene dicarboxylic acid. Thus the development of a process for industrially producing 2,6-DMN is eagerly desired. The aforesaid Japanese Patent Application Laid-Open No. 134634/1974 also discloses a process for producing 5-(p-totyl)-penta-2-ene from p-xylene and butadine. In this case, it is presumed that 1,7-DMN is obtained by the successive cyclization and dehydrogenation, 2,7-DMN is obtained in high purity by further isomerization and crystallization, and also the use of m-xylene enables the production of the mixture of 1,6-DMN and 1,8-DMN.

It can be said that the process for producing DMN by the use of xylene and butadiene as starting raw materials is industrially excellent, since it enables the production of a specific DMN with isomerically high purity as described hereinbefore.

The process for producing DMN from xylene and butadiene comprises the steps of synthesizing 5-tolyl-penta-2-ene by side-chain alkenylation, synthesizing dimethyltetralin by means of cyclization, synthesizing DMN by means of dehydrogenation, isomerizing DMN and crystallizing isolation. The synthesis of dimethyltetralin by cyclizing 5-tolyl-penta-2-ene is disclosed in Japanese Patent Application Laid-Open No. 93348/1974 in which is used a solid phosphoric acid as the catalyst and Published International Patent Application No. 500052/1991 in which is employed as the catalyst a ultra-stabilized Y-type zeolite that is modified with platinum and copper, showing a yield of 95% or more in the working examples of both the disclosures. The synthesis of DMN by dehydrogenating dimethyltetralin is disclosed in Japanese Patent Application Laid-Open Nos. 76852/1973 and 67261/1973 in which are used as the catalysts chromia-alumina and palladium with rhenium supported on a carrier, respectively, showing a yield of 95% or more in the wording examples of both the disclosures.

In addition to the high yield attained in both the cyclization and dehydrogenation steps, an attempt is made to simultaneously effect cyclization and dehydrogenation reactions, exemplified by Japanese Patent Application Laid Open No. 31151/1975 in which DMN is produced by cyclizing dehydrogenizing 5-(o-tolyl)-penta-2-ene by the use of a chromina-supporting silica-alumina based catalyst at a conversion efficiency of 97% and a DMN yield of 75% as the working example. There are also disclosed in Japanese Patent Application Laid-Open Nos. 1036/1975, 1037/1975 and 17983/1975, processes for producing DMN by cyclizing dehydrogenating 5-(o-tolyl)-penta-2-ene by the use of palladium supported on alumina or activated carbon, the combination of palladium, rhodium and rhenium supported on silica-alumina, and platinum supported on silica-alumina, respectively as the catalyst. However, in each of the working examples of the aforementioned disclosures, DMN yield is only 60% at the maximum. As is seen from the above, the two-stage process in which cyclization and dehydrogenation reactions are carried out separately attains an overall yield of 90% or more through both the reactions; while the single-stage process in which cyclization and dehydrogenation reactions are effected simultaneously attains a yield of 75% at the most. In view of the reaction performance, the two-stage process is superior to the single-stage process. Nevertheless, if a single-stage process is materialized which attains a yield comparable to that by a two-stage process, it is greatly advantageous from the industrial viewpoint in that the production process can be simplified.

In addition, the cyclization reaction is an exothermic reaction accompanied by a great reaction heat of 20 kcal/mol, causing a serious problem in the process of how to remove the reaction heat. On the contrary, the dehydrogenation reaction is an endothermic reaction accompanied with a great heat absorption of about 30 kcal/mol, bringing about a serious problem in the process of how to supply the required heat, fundamentally different from the cyclization reaction. Accordingly, the materialization of the effective single-stage process capable of simultaneously proceeding with both the reactions, if possible, greatly favors the effective utilization of reaction heat and heat engineering in addition to the process simplification.

For example, in the process for producing a specific DMN from xylene and butadiene in a multistage steps, the conventional technique of preparing DMN from the corresponding 5-tolyl-penta-2-ene formed by side-chains alkenylation requires two-stage reactions in view of the reaction performance including the cyclization of 5-tolyl-penta-2-ene into dimethyltralin, followed by dehydrogenation thereof into the corresponding DMN. If the cyclization dehydrogenation step incorporating both the reactions can be realized, it enables process simplification, effective utilization of reaction heat and rationalization of heat balance, thereby enhancing the industrial significance of itself. Thus, there is desired the development of an effective process for converting 5-tolyl-penta-2-ene into the corresponding DMN by single-stage cyclization dehydrogenation reactions.

The catalyst for converting 5-tolyl-penta-2-ene into the corresponding DMN in single stage synthesis needs to be endowed with both cyclizing and dehydrogenating functions. It is possible to cyclize 5-tolyl-penta-2-ene by the use of a solid catalyst such as solid phosphoric acid, zeolite and silica-alumina. However, a simple combination of the above-mentioned solid catalyst with the dehydrogenation catalyst typified by platinum, rhenium, palladium, rhodium, chromia-alumina, etc. can not constitute an effective cyclization dehydrogenation catalyst. It is clear from the fact that a high cyclization dehydrogenation yield is not achieved in Japanese Patent Publication No. 31151/1975 wherein chromia is supported on silica-alumina catalyst and in Japanese Patent Publication Nos. 1036/1975, 1037/1975 and 17983/1975 wherein the catalysts each comprising palladium rhodium, rhenium or platinum supported or alumina, silica-alumina or activated carbon are employed.

Moreover, only a low cyclization dehydrogenation yield is obtained even by the use of the catalyst comprising the component having a high dehydrogenating function such as palladium, rhenium, rhodium or platinum supported on the solid acid catalyst that is effective for cyclization reaction such as X-type zeolite, ultra-stabilized Y-type zeolite (hereinafter referred to as "USY"), Y-type zeolite or alumina in cyclizing 5-tolyl-penta-2-ene. It is presumed to be due to the fact that the conventional supporting method cannot increase the noble-metal supporting quantity of the resultant catalyst, thereby failing to enhance the dehydrogenating function of the catalyst. Although it is possible to enhance the dehydrogenating function to some extent by raising the reaction temperature in the aforesaid method, the elevated temperature causes decomposition and polymerization during the reaction, resulting in failure to improve the cyclization dehydrogenation yield. In other words, the catalyst of the conventional supporting system is devoid of the balance among various catalytic functions of the prepared catalyst including cyclizing activity, dehydrogenating activity, decomposing activity and polymerizing activity, thus making itself unsuitable for the objective cyclization dehydrogenation of 5-tolyl-penta-2-ene. The failure to attain a high cyclizing dehydrogenating function by the simple combination of a cyclization catalyst with a dehydrogenation catalyst is attributable also to the great difference between the reaction conditions effective for cyclization regarding reaction pressure, reaction temperature and contact time and the reaction conditions effective for dehydrogenation.

SUMMARY OF THE INVENTION

It is an object of the present invention to provide a process for producing DMN from the corresponding 5-tolyl-penta-2-ene in high yield by single-stage step.

It is another object of the present invention to provide a method of simplifying the steps, utilizing the reaction heat and rationalizing the heat balance during the production of DMN.

It is still another object of the present invention to provide a catalyst effective for producing DMN from the corresponding 5-tolyl-penta-2-ene by single-stage step.

Other objects of the present invention will be obvious from the description of this text hereinafter disclosed.

On the basis of the above-mentioned objects, investigation was concentrated by the present inventors on a catalyst capable of providing DMN in high yield by cyclizing dehydrogenating 5-tolyl-penta-2-ene into the corresponding DMN. During the course of the investigation, particular attention was paid by them to the effectiveness of preparing a catalyst having high cyclizing dehydrogenating functions by combining the cyclizing function of a solid-acid catalyst with the dehydrogenating function of a noble-metal catalyst. On the basis of the concept, a trial was made by them to prepare such catalyst by selecting as the solid-acid crystalline aluminosilicate, alumina or silica-alumina and as the noble metal palladium or platinum, adding thereto a substantially inert carrier to sufficiently disperse therein and simultaneously adjusting the ratio by weight of the solid-acid component to the palladium and/or platinum component. As a result, the trial led to success in simultaneously proceeding with cyclization dehydrogenation reactions, thereby developing a catalyst substantially free from side reaction such as decomposition or polymerization throughout the reaction. The present investigation was accomplished on the basis of the above-mentioned finding and information.

Specifically, the present invention provides a process for producing dimethylnaphthalene which comprises cyclizing dehydrogenating 5-tolyl-penta-2-ene in the presence of a catalyst comprising in combination (a) at least one member selected from crystalline aluminosilicate, silica-alumina and alumina; (b) at least one member selected from palladium and platinum; and a carrier.

DESCRIPTION OF PREFERRED EMBODIMENTS

As described hereinbefore, the catalyst to be used in the present invention comprises as indispensable constituents (a) crystalline aluminosilicate, alumina, silica-alumina or a mixture thereof; (b) palladium and/or platinum; and a carrier.

Solid phosphoric acid and a heteropolyacid are effective for the cyclization of 5-tolyl-penta-2-ene but unsuitable as the catalyst for the cyclization dehydrogenation thereof when combined with the noble metal. By the use of (a) crystalline aluminosilicate, alumina, silica-alumina or a mixture thereof and by the combination thereof with (b) a noble metal, that is, palladium and/or platinum in the present invention, there is obtained the cyclization dehydrogenation catalyst for 5-tolyl-penta-2-ene. Among the possible nobel metals, rhenium an rhodium have each an extremely high dehydrogenating function but are unsuitable for composing a cyclization dehydrogenation catalyst for 5-tolyl-penta-2-ene in combination with a solid acid. In the present invention, therefore, the cyclization dehydrogenation catalyst for 5-tolyl-penta-2-ene can be composed of (b) palladium and/or platinum as the noble metal components and by the combination thereof with the above-mentioned (a) component, that is, the solid acid.

As the crystalline aluminosilicate to be employed in the present invention, there may be used publicly known ones such as mordenite, X-type zeolite and Y-type zeolite, among which are particularly desirable mordenite, Y-type zeolite and USY.

With regard to (b) palladium and/or platinum as the noble metal component, various compounds are available insofar as the aforementioned metallic component is contained therein and specifically exemplified by as palladium component, palladium chloride, tetraamminepalladium nitrate, diamminedinitropalladium and bis-acetylacetonato-palladium in addition to metallic palladium and as platinum component, chloroplatinic acid, tetraammineplatinum acetate, diamminedinitroplatinum and bis-acetylacetonato-platinum.

The mixing ratio by weight of (a) at least one solid acid selected from crystalline aluminosilicate, alumina and silica-alumina to (b) the noble metal comprising palladium and/or platinum varies depending upon the content and strength of the aforementioned solid acid, but is usually 0.1 to 10, preferably 0.2 to 10 . An excessive amount of the aforesaid (a) solid acid results in susceptibility to the side reaction such as isomerization, decomposition and polymerization, whereas an unreasonably low amount thereof lowers the reactivity of 5-tolyl-penta-2-ene.

The carrier to be employed for the catalyst in the present invention is preferably a carrier which sufficiently disperses the components other than the carrier, especially (b) palladium and/or platinum and which has a low reactivity with 5-tolyl-penta-2-ene. However, a strongly acidic carrier such as activated alumina is unfavorable, since it is apt to cause such side reactions as polymerization and decomposition. Examples of preferable carriers include non-acidic or weekly acidic ones such as carbon, silicon oxide, titanium oxide and zirconium oxide. The amount of the carrier to be used is related principally to the amount of (b) palladium and/or platinum as the noble metal, and is usually 10 to 200 times, preferably 15 to 100 time by weight based on the aforestated (b) noble metal. An amount of the carrier less than 10 times by weight the amount of the (b) noble metal unfavorably worsens the dispersion of palladium and/or platinum as the noble metal component.

The method of preparing the catalyst according to the present invention is not specifically limited insofar as the above-mentioned (a) solid acid and (b) nobel metal are sufficiently dispersed in the catalyst by the aforesaid method.

Examples of the adoptable methods include (1) a method which comprises supporting on a carrier, (b) palladium and/or platinum as the noble metal component and mixing it with (a) at least one solid-acid component selected from crystalline aluminosilicate, alumina and silica-alumina to prepare the catalyst; (2) a method which comprises mixing (a) at least one solid-acid component selected from crystalline aluminosilicate, alumina and silica-alumina with a carrier to prepare the catalyst and supporting (b) palladium and/or platinum as the noble metal component on the catalyst thus prepared; and (3) a method which comprises simultaneously mixing (a) at least one solid-acid component selected from crystalline aluminosilicate, alumina and silica-alumina, (b) compound(s) of palladium or platinum as the noble metal component and a carrier to prepare a catalyst.

The reaction process applicable to the cyclization dehydrogenation reaction of 5-tolyl-penta-2-ene by the use of the catalyst of the present invention is not specifically limited but is exemplified by a batch-wise system and a continuous system. Likewise, the acceptable reaction equipment is not specifically limited but is exemplified by a fixed bed, a moving bed and a fluidized bed, among which however, is preferable a fixed-bed flow system in view of operational convenience.

The reaction temperature is usually in the range of 150° to 400° C., preferably 200° to 300° C. In order to prevent the hydrogen produced by cyclization dehydrogenation reaction from causing the reaction at the same time by which the raw material 5-tolyl-penta-2-ene is hydrogenated, an inert gas is preferably allowed to coexist therewith and is desirably exemplified by nitrogen, steam and carbon dioxde gas. Since the objective DMN is in the form of a solid at room temperature, the starting raw material is preferably diluted with a proper solvent prior to the reaction for operational convenience. In this case a solvent may be used in place of an inert gas. Such solvent is preferably stable under the reaction conditions and capable of sufficiently dissolving the resultant DMN, such solvent being exemplified by an aromatic hydrocarbon such as benzene and toluene and a saturated aliphatic hydrocarbon such as heptane and hexane.

In the case of cyclizing dehydrogenating 5-tolyl-penta-2-ene according to the present invention, there are obtained in high yield DMN comprising as the principal component 1,5-DMN, 1,7-DMN and 1,6-DMN along with 1,8-DMN when the starting raw materials are 5-(o-tolyl)-penta-2-ene, 5-(p-tolyl)-penta-2-ene and 5-(m-tolyl)-penta-2-ene, respectively.

DMN comprising 1,5-DMN as the principal component that is obtained in the case where the starting raw material is 5-(o-tolyl)-penta-2-ene consists essentially of 1,5-DMN, 1,6-DMN and 2,6-DMN. The resultant three kinds of isomers belong to the same group with respect to isomerization and therefore, 2,6-DMN can be collected with ease by isomerizing the isomer mixture followed by separation thereof through crystallization.

DMN comprising 1,7-DMN as the primary component that is obtained when the starting raw material is 5-(p-tolyl)-penta-2-ene consists essentially of 1,7-DMN, 1,8-DMN, and 2,7-DMN. The resultant three kinds of isomers belong to the same group with regard to isomerizaion and therefore, 2,7-DMN can be collected with ease by isomerizing the isomer mixture followed by separation thereof through crystalization.

The process for producing DMN in high yield by single-step reaction from the corresponding 5-tolyl-penta-2-ene as the starting raw material has been developed according to the present invention. Different from the conventional process requiring two-step reactions, the above-developed process of the present invention is simplified in equipment and operation, thereby enhancing the industrial significance of itself.

In the following, the present invention will be described in more detail with reference to examples and comparative examples. (1) With regard to Examples 1 to 10 and Comparative Examples 1 to 5, a quartz-made tubular reactor with 20 mm inside diameter was packed inside with 20 g of the catalyst as prepared in the relevant example or comparative example as described hereunder, in which 30% by weight of a solution of 5-(o-tolyl)-penta-2-ene as the starting raw material in heptane was subjected to cyclization dehydrogenation reaction at atmospheric pressure at a temperature of 250° to 300° C. at feed rates of 80 g/hr of the solution and 500 cc/min of nitrogen. The results obtained are given in Table 1.

In each of the examples and comparative examples, the conversion of 5-(o-tolyl)-penta-2-ene used as the starting raw material indicated 100% without any exception. The catalysts as prepared in the aforesaid examples resulted in high yield of DMN as well as high yield of 1,5-DMN in total DMN. As opposed to the above, the catalysts as prepared in the aforesaid comparative examples led to low yield of DMN, thus demonstrating a marked superiority of the catalyst according to the present invention.

(2) With respect to Example 11 and Comparative Examples 6 and 7, the experimental test was carried out according to the procedure as described in the relevant example or comparative example.

Of course, the present invention shall not be limited to any of the examples.

EXAMPLE 1

In a vessel made of stainless steel were placed 15 g of mordenite available in the market, 5% by weight of palladium supported on 270 g of activated carbon and 21 g of alumina sol containing 70% by weight of alumina as the binder, and the resultant mixture was incorporated with 500 g of pure water with vigorous stirring and mixing at room temperature. The resultant product was molded with an extruding molding machine, dried at 110° C. and calcined at 350° C. for 3 hours to prepare a catalyst, which was used for the reaction.

EXAMPLE 2

The procedure in Example 1 was repeated to prepare a catalyst, which was used for the reaction, except that there were used 10 g of mordenite available in the market and one (1) % by weight of palladium supported on 320 g of activated carbon.

EXAMPLE 3

The procedure in Example 1 was repeated to prepare a catalyst, which was used for the reaction, except that there were used 10 g of USY zeolite available in the market, 2% by weight of palladium supported on 550 g of activated carbon, and 41 g of alumina sol containing 70% by weight of alumina.

EXAMPLE 4

The procedure in Example 1 was repeated to prepare a catalyst, which was used for the reaction, except that there were used 10 g of USY zeolite available in the market, 5% by weight of palladium supported on 550 g of silica and 160 g of silica sol containing 25% by weight of silica without the addition of pure water.

EXAMPLE 5

The procedure in Example 1 was repeated to prepare a catalyst, which was used for the reaction, except that there were used 10 g of USY zeolite available in the market, 2% by weight of platinum supported on 550 g of silica and 41 g of aluminasol containing 70% by weight of alumina.

EXAMPLE 6

The procedure in Example 1 was repeated to prepare a catalyst, which was used for the reaction, except that there were used 15 g of Y-type zeolite available in the market in place of 15 g of mordenite, 2% by weight of platinum supported on 200 g of activated carbon in place of 5% by weight of palladium supported on 270 g of activated carbon.

EXAMPLE 7

The procedure in Example 1 was repeated to prepare a catalyst, which was used for the reaction, except that there were used 45 g of silica-alumina available in the market, 2% by weight of palladium supported on 250 g of activated carbon and 120 g of silica sol containing 25% by weight of silica without the addition of pure water.

EXAMPLE 8

The procedure in Example 1 was repeated to prepare a catalyst, which was used for the reaction, except that there was used 5% by weight of palladium supported on titania in place of 5% by weight of palladium supported on activated carbon.

EXAMPLE 9

The procedure in Example 1 was repeated to prepare a catalyst, which was used for the reaction, except that there was used 2% by weight of platinum supported on zirconia in place of 5% by weight of palladium supported on activated carbon.

EXAMPLE 10

In a vessel made of stainless steel were placed 10 g of H-type mordenite available in the market, 500 g of silica-gel, and 30 g of alumina sol containing 70% by weigh of alumina, and the resultant mixture was incorporated with 700 g of pure water with sufficient stirring and mixing at room temperature. The resultant product was molded with an extruding molding machine, dried at 110° C. and fired at 350° C. for 3 hours. The obtained molding in an amount of 100 g was added to 0.1N solution of 2.65 g of chloroplatinic acid in aqueous hydrochloric acid to impregnate under stirring at 50° C. for 2 hours and dried at 110° C. Then, the impregnated molding was calcined at 550° C. for 2 hours and thereafter reduced with hydrogen to produce a catalyst, which was used for the reaction.

COMPARATIVE EXAMPLE 1

The procedure in Example 3 was repeated to prepare a catalyst, which was used for the reaction, except that there was used 2% by weight of palladium supported on alumina in place of 2% by weight of palladium supported on activated carbon.

COMPARATIVE EXAMPLE 2

The procedure in Example 1 was repeated to prepare a catalyst, which was used for the reaction, except that there were used 70 g of mordenite, 5% by weight of palladium supported on 140 g of activated carbon, and 33 g of alumina sol containing 70% by weight of alumina.

COMPARATIVE EXAMPLE 3

The procedure in Example 3 was repeated to prepare a catalyst, which was used for the reaction, except that there was used 2% by weight of rhenium supported on activated carbon.

COMPARATIVE EXAMPLE 4

The procedure in Example 3 was repeated to prepare a catalyst, which was used for the reaction, except that there was used 2% by weight of rhodium supported on activated carbon.

COMPARATIVE EXAMPLE 5

The procedure in Example 11 was repeated to prepare a catalyst, which was used for the reaction, except that there were used 240 g of mordenite, 14 g of alumina sol and 300 g of pure water without the use of silica.

COMPARATIVE EXAMPLE 6

The starting raw material of 5-(o-tolyl)-penta-2-ene was subjected to cyclization dehydrogenation reaction by the use of 2% by weight of palladium supported on 20 g of activated carbon as such under the reaction method and conditions same as those in the above-mentioned examples and comparative examples but at a reaction temperature of 300° C. As a results, the conversion of the 5-(o-tolyl)-penta-2-ene was as low as 62%. The major reaction products were indanes and hydrogenated products from the starting raw material, and the formation of DMN was hardly recognized.

COMPARATIVE EXAMPLE 7

The starting raw material of 5-(o-tolyl)-penta-2-ene was subjected the cyclization dehydrogenation reaction by the use of 20 g of USY available in the market as such under the reaction method and conditions same as those in the above-mentioned examples and comparative examples but at a reaction temperature of 260° C. As a result, the conversion of the 5-(o-tolyl)-penta-2-ene was 100%. However, the major cyclized products were dimethyltetralin and the like and the yield of DMN was not more than 10%. In the case of reaction temperature being 300° C., remarkable side reactions were caused including the formation of indane, decomposition and polymerization, thus lowering the yield of DMN to 10% or lower.

EXAMPLE 11

The procedure in Example 1 was repeated except that 5-(p-tolyl)-penta-2-ene was used in place of 5-(o-tolyl)-penta-2-ene. The results are given in Table 1. The conversion of 5-(p-tolyl)-penta-2-ene was 100%.

TABLE 1

| No. | Reaction temperature (°C.) | Composition of resultant reaction liquid (wt %) | | | | | | Hydorgenated matter in starting material |
|---|---|---|---|---|---|---|---|---|
| | | DMN | Isomer concentration in DMN | | | | DMT | |
| | | | 1,5- | 1,6- | 2,6- | Others | | |
| Example 1 | 260 | 91.2 | 91.4 | 6.1 | 2.5 | 0 | 3.2 | 3.7 |
| Example 2 | 250 | 85.5 | 83.9 | 12.2 | 3.8 | 0.1 | 5.3 | 3.9 |
| Example 3 | 250 | 90.3 | 88.2 | 8.4 | 3.4 | 0 | 4.5 | 2.8 |
| Exa,ple 4 | 280 | 88.4 | 93.0 | 4.6 | 2.4 | 0 | 4.2 | 3.0 |
| Example 5 | 270 | 88.2 | 90.4 | 7.1 | 2.5 | 0 | 4.6 | 3.9 |
| Example 6 | 270 | 90.0 | 87.8 | 6.9 | 5.3 | 0 | 3.8 | 4.1 |
| Example 7 | 280 | 86.3 | 81.8 | 2.2 | 5.8 | 0.2 | 4.3 | 3.8 |
| Example 8 | 260 | 89.3 | 90.3 | 6.9 | 2.8 | 0 | 4.4 | 3.9 |
| Example 9 | 260 | 90.3 | 88.0 | 7.8 | 4.2 | 0 | 3.6 | 4.0 |
| Example 10 | 260 | 90.8 | 92.6 | 4.6 | 2.8 | 0 | 5.2 | 2.8 |
| Comparative Example 1 | 280 | 7.6 | 56.6 | 18.7 | 8.4 | 16.3 | 68.9 | 7.4 |
| Comparative Example 2 | 300 | 51.6 | 36.5 | 24.1 | 18.4 | 21.0 | 38.5 | 3.7 |
| Comparative Example 3 | 260 | 24.1 | 80.3 | 13.4 | 6.1 | 0.2 | 67.3 | 2.0 |
| Comparative | 260 | 34.3 | 77.0 | 14.9 | 7.8 | 0.3 | 57.9 | 2.8 |

TABLE 1-continued

| No. | Reaction temperature (°C.) | Composition of resultant reaction liquid (wt %) | | | | | | |
|---|---|---|---|---|---|---|---|---|
| | | DMN | Isomer concentration in DMN | | | | DMT | Hydorgenated matter in starting material |
| | | | 1,5- | 1,6- | 2,6- | Others | | |
| Example 4 Comparative | 280 | 4.8 | 48.3 | 21.5 | 11.8 | 18.4 | 62.3 | 11.0 |
| Example 5 Comparative | 300 | 0.6 | — | — | — | — | 4.3 | 23.3 |
| Example 6 Comparative | 260 | 3.1 | 29.3 | 43.2 | 20.1 | 7.4 | 81.5 | 0.3 |
| Example 7 | 300 | 9.0 | 27.2 | 33.3 | 18.7 | 20.8 | 51.3 | 0.8 |
| Example 11 | 260 | 90.7 | 91.2 | 5.3 | 3.5 | 0 | 3.4 | 3.9 |
| | | | (1,7- | 2,7- | 1,8- | Others) | | |

(Remark) DMT: Dimethyltetralin

What is claimed is:

1. A process for producing dimethylnaphthalene which comprises cyclizing and dehydrogenating 5-tolyl-penta-2-ene in the presence of a catalyst comprising in combination (a) at least one solid acid selected from the group consisting of mordenite, X-zeolite, Y-zeolite, silica-alumina and alumina; (b) at least one member selected from the group consisting of palladium and platinum, wherein the ratio by weight of said (a) at least one solid acid to said (b) at least one member selected from the group consisting of palladium and platinum is 0.1 to 10; and (c) at least one non-acidic carrier selected from the group consisting of carbon, silicon oxide, titanium oxide and zirconium oxide.

2. The process according to claim 1 wherein the ratio by weight of the carrier (c) to the (b) at least one member selected from the group consisting of palladium and platinum is 10 to 200.

3. The process according to claim 1 wherein said solid acid is selected from the group consisting of mordenite, X-zeolite and Y-zeolite.

4. The process according to claim 1 wherein the process is carried out at a temperature of 150° to 400° C.

5. The process according to claim 1 wherein the 5-tolyl-penta-2-ene is 5-(o-tolyl)-penta-2-ene and the dimethylnaphthalene obtained comprises 1,5-dimethylnaphthalene as the principal component.

6. The process according to claim 1 wherein the 5-tolyl-penta-2-ene is 5-(p-tolyl)-penta-2-ene and the dimethylnaphthalene obtained comprises 1,7-dimethylnaphthalene as the principal component.

7. The process according to claim 1 wherein the 5-tolyl-penta-2-ene is 5-(m-tolyl)-penta-2-ene and the dimethylnaphthalene obtained comprises 1,6- and 1,8-dimethylnaphthalene as the principal components.

8. The process according to claim 1, wherein said solid acid is ultra-stabilized Y-zeolite.

9. The process according to claim 1 wherein the ratio by weight of said solid acid to said palladium or platinum is 0.2 to 10.

10. The process according to claim 1 wherein the ratio by weight of said carrier to said palladium or platinum is 15 to 100.

11. The process according to claim 10 wherein the process is carried out at a temperature of 150° to 400° C.

12. The process according to claim 10 wherein the process is carried at a temperature of 200° to 300° C.

13. The process according to claim 12 wherein said solid acid is selected from the group consisting of mordenite, X-zeolite and Y-zeolite.

14. The process according to claim 12 wherein said solid acid is ultra-stabilized Y-zeolite.

15. The process according to claim 13 wherein the 5-tolyl-penta-2-ene is 5(o-tolyl) -penta-2-ene.

16. The process according to claim 15 wherein the dimethylnaphthalene obtained comprises predominately 1,5-dimethylnaphthalene.

17. The process according to claim 13 wherein the 5-tolyl-penta-2-ene is 5-(p-tolyl)-penta-2-ene and the dimethylnaphthalene obtained comprises predominantly 1,7-dimethylnaphthalene.

18. The process according to claim 13 wherein the 5-tolyl-penta-2-ene is 5-(m-tolyl)-penta-2-ene and the dimethylnaphthalene obtained comprises predominantly 1,6-dimethylnaphthalene and 1,8-dimethylnaphthalene.

* * * * *